United States Patent [19]

Fields et al.

[11] 4,157,431

[45] Jun. 5, 1979

[54] SEPARATION OF BLOOD COAGULATION FACTORS WITH NON-ACTIVATING POLYELECTROLYTES

[75] Inventors: Joseph E. Fields, Ballwin; Robert J. Slocombe, St. Louis, both of Mo.

[73] Assignee: Monsanto Company, St. Louis, Mo.

[21] Appl. No.: 933,698

[22] Filed: Aug. 15, 1978

Related U.S. Application Data

[63] Continuation-in-part of Ser. No. 818,918, Jul. 25, 1977, abandoned.

[51] Int. Cl.$^2$ ............................ C08F 8/32; C07G 7/00
[52] U.S. Cl. .................................. 526/15; 260/112 B; 260/122; 424/101; 424/177; 526/50; 526/52.2; 526/52.5
[58] Field of Search .............. 260/112 B, 122; 526/15, 526/50, 52.2, 52.5

[56] References Cited

U.S. PATENT DOCUMENTS

| | | | |
|---|---|---|---|
| 3,157,595 | 11/1964 | Johnson et al. | 210/54 |
| 3,340,680 | 9/1967 | Fields et al. | 55/22 |
| 3,554,985 | 1/1971 | Fields et al. | 260/78.5 |
| 3,555,001 | 1/1971 | Wallis et al. | 260/112 |
| 3,651,213 | 3/1972 | Wallis et al. | 424/89 |
| 3,655,509 | 4/1972 | Fields et al. | 195/1.5 |
| 3,682,881 | 8/1972 | Fekete et al. | 260/112 B |

*Primary Examiner*—Stanford M. Levin
*Attorney, Agent, or Firm*—Scott J. Meyer; James W. Williams, Jr.

[57] ABSTRACT

Blood coagulation factors such as Factor VIII are separated from admixture with other blood proteins without producing activation of said coagulation factors by contacting with a water-insoluble, cross-linked polyelectrolyte copolymer of (a) $C_{2-18}$ unsaturated monomer and (b) $C_{4-12}$ unsaturated polycarboxylic acid or anhydride which is partially substituted at its free carboxyl or anhydride sites with amine-imides and in which substantially all the remaining free carboxyl or anhydride sites are blocked with alkoxyalkylamine to form alkoxyalkylimide units.

22 Claims, No Drawings

SEPARATION OF BLOOD COAGULATION FACTORS WITH NON-ACTIVATING POLYELECTROLYTES

CROSS-REFERENCE TO RELATED CASE

This is a continuation-in-part of application Ser. No. 818,918, filed July 25, 1977, now abandoned.

BACKGROUND OF THE INVENTION

This invention relates to blood fractionation and more particularly to the fractionation of blood coagulation factors with certain unique polyelectrolytes.

The process of blood coagulation is a complicated physiological activity that involves the interaction of numerous substances found in normal whole blood. It is known that certain factors associated with the blood coagulation mechanism are absent or seriously deficient in certain individuals. Thus, in those patients suffering from classical hemophilia, antihemophilic factor A (AHF, Factor VIII) is deficient. In those patients suffering from hemophilia B, plasma thromboplastin component (PTC, Factor IX) is missing from the blood. A small percentage of hemophiliacs also are lacking in the so-called Von Willebrand's Factor which is related to Factor VIII. Several other factors which are important in the coagulation mechanism, the absence of which can also lead to bleeding disorders, are, for example, Factors II, VII and X. The latter three factors together with Factor IX are frequently referred to as the prothrombin complex factors.

In the development of modern blood banking programs involving the collection and storage of large quantities of blood and blood components, the establishment of adequate preservation systems is critical. Since World War II it has been common practice to collect blood in a solution of citric acid, sodium citrate and dextrose, known as ACD blood. The problem of preserving blood is much simplified, however, when it is reduced to preservation of various blood components since it is easier to meet the environmental requirements of the separate components than of whole blood.

Moreover, it is wasteful and even detrimental to the patient to administer more blood components than required. Thus, the hemophiliac needing certain blood coagulation factors ideally should be given only those factors required or at least a purified concentrate of those factors.

The fractionation of blood coagulation factors, particularly Factor VIII and those factors associated with the prothrombin complex, is well-known, as can be seen from U.S. Pat. No. 3,682,881 and numerous other patents and publications. Various materials used in such fractionation are, for example, barium sulfate, aluminum hydroxide, polyethylene glycol, rivanol (6,9-diamino 2-ethoxyacridine lactate), glycine, DEAE-cellulose and DEAE-Sephadex.

Another group of substances which have been found useful in the fractionation of blood components are the water-insoluble, cross-linked polyelectrolyte copolymers described in U.S. Pat. No. 3,554,985. These substances are described as cross-linked copolymers of an (a) unsaturated monomer of 2 to 12 carbon atoms and (b) a monomer selected from the group consisting of (1) a mixture of an unsaturated polycarboxylic acid or anhydride and an unsaturated polycarboxylic acid amine-imide, and (2) an unsaturated polycarboxylic acid amine-imide, the polymeric units containing a defined minimum percentage of an amine-imide group which is a diloweralkylaminoloweralkylimide group wherein loweralkyl has 1 to 5 carbon atoms. Each of the polymeric units contains reactive sites in the form of an anhydride group or two carboxyl groups or derivatives of these groups. At least 3 percent of these reactive sites are said to be converted to the diloweralkylaminoloweralkylimide. The polyelectrolyte copolymers are thus generally only partially substituted with amine-imides.

The foregoing polyelectrolyte copolymers are known to be useful for preparation of various blood components such as albumin, gamma globulin, lipoproteins, hemoglobin and anti-trypsin factor as described in U.S. Pat. No. 3,555,001. In the fractionation of these components, the adsorption of a charged protein species to a charged insoluble substrate surface is accomplished through electrostatic interactions between sites of opposite charges, and this in turn is related to the isoelectric pH (IEpH) of the protein species and the pH of the medium.

In the fractionation of coagulation factors, such as Factor VIII, with certain of the polyelectrolytes described in U.S. Pat. Nos. 3,555,001 and 3,554,985, it has been found that use of the separated blood factor in standard clotting time tests causes a marked reduction in clotting time. This pre-activation of the separated Factor VIII component represents a serious deficiency in the clinical usefulness of this material. Such preactivation has also been observed by reaction in dogs when the separated Factor VIII was injected intravenously in the dogs. These reactions consisted of:

(1) a behavior change whereby the dog rotates in its cage for 24 hours, (2) a hemolysis reaction evidenced by hemoglobinuria, and (3) a maked lowering of blood platelet count accompanied by rise in blood pressure.

This pre-activation has been found to be related to the structure and composition of the adsorbing polyelectrolyte in which there may be free hydroxyl groups capable of hydrogen bonding reactions. Thus, the polyelectrolyte copolymer may include the following polymeric structural units:

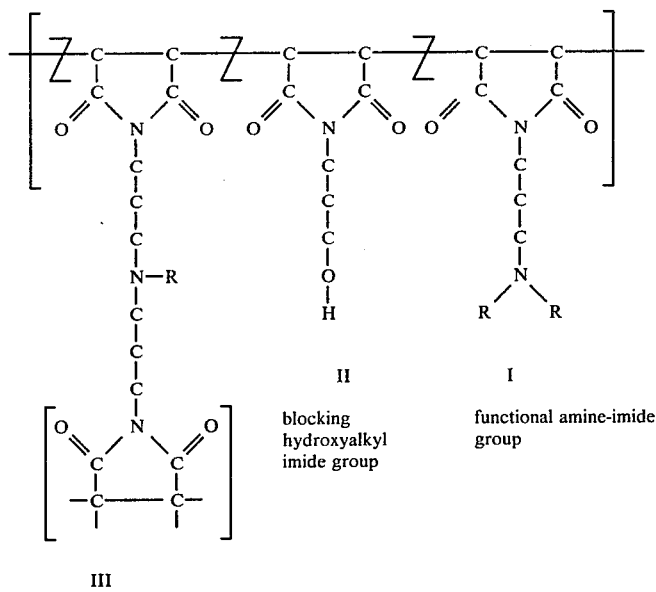

II blocking hydroxyalkyl imide group

I functional amine-imide group

III crosslinking group

R = alkyl having from 1 to 5 carbon atoms
Z = bivalent hydrocarbon radical having from 2 to 18 carbon atoms U.S. Pat. No. 3,555,001 discloses that the polyelectrolyte may possess from 2–100% amine-imide linkages, with the remaining carboxyl groups being in the anhydride form (col. 5, lines 29–31). It is further stated that the residual, non-modified polymer anhydride units may be converted to neutral groups or units by reaction of the unreacted anhydride units with compounds such as alkylamines, aminoalcohols and alcohols (col. 5, lines 54–60). In the illustrative formula, above, said partial substitution with the functional amine-imide likages is shown at I, the cross-linking imino-imide linkages are shown at III, and the remaining free carboxyl groups in the anhydride form are shown to be converted to neutral groups by blocking or reaction with an aminoalcohol at II thereby giving rise to hydroxyalkylimide units.

Notwithstanding the foregoing blocking of residual, free anhydride groups with aminoalcohol at II, it has been found that the free hydroxyls thus introduced on the polymer backbone in the form of hydroxyalkylimide groups as shown at II in the above formula contribute to the aforesaid pre-activation of Factor VIII which has been fractionated with this type of polyelectrolyte.

It has been further found that the pre-formation of the salt form of this type of polyelectrolyte, for example the hydrochloride salt, further accentuates the aforesaid pre-activation. Although the free amine form does not necessarily produce activation, the salt form of the polyelectrolyte is preferred from the standpoint of stability and the processing ability to remove water soluble extractable material which could find its way into the fractionated blood component.

Although the inventors are not bound by theory, it is believed that the above activation of Factor VIII may be due, in part, to the presence of plasma zymogens or enzymes resulting from zymogen activation in the separated Factor VIII fraction. These zymogens are known to be activated by negatively charged surfaces or hydroxylated surfaces capable of hydrogen bonding such as collagen. The aforesaid polymers having the free hydroxyl are capable of intra- and interchain hydrogen bonding with proteins with resultant areas of partial negative charge. In order to overcome this overall process of activation, the present inventors have synthesized new polyelectrolytes of the foregoing general type having partial substitution with amine-imides in which all the remaining free anhydrides are blocked with non-activating groups.

SUMMARY OF THE INVENTION

In accordance with the present invention, polyelectrolytes of the general type described hereinbefore which are partially substituted at the free carboxyl or anhydride sites with amine-imides are modified in structure whereby they can be used for the fractionation of coagulation factors, especially Factor VIII, without producing any substantial pre-activation of the coagulation factors. Briefly stated, this modification consists in blocking substantially all the remaining free carboxyl or anhydride sites with alkoxyalkylamine. This pre-activation of coagulation factors is thereby avoided irrespective of whether the free amine form or the salt form of the polyelectrolyte is used. As used herein, the partial substitution with amine-imides means from about 2% to about 98% substitution and generally is less than about 90% substitution.

DETAILED DESCRIPTION OF THE INVENTION

In the present invention, several embodiments of the non-activating polyelectrolytes are contemplated by the inventors. While the specification concludes with claims particularly pointing out and distinctly claiming the subject matter regarded as forming the invention, it is believed that the invention and its advantages will be better understood from the following description of the preferred embodiments.

In general, the polyelectrolytes which can be modified by blocking of the anhydride groups on the polymer backbone in accordance with this invention include those disclosed in the aforementioned U.S. Pat. Nos. 3,554,985 and 3,555,001, said patents being incorporated herein by reference. For purposes of convenience, the polymers described in said patents will be referred to as EMA-type polymers (ethylene/maleic anhydride or acid). These polymers are illustrated by the general examples in the following sections I and II:

I

The polycarboxylic acid polymers can be of the non-vicinal-type including those containing monomer units, such as acrylic acid, acrylic anhydride, methacrylic acid, crotonic acid or their respective derivatives, including partial salts, amides and esters or of the vicinal type, including maleic, itaconic, citraconic, α-dimethyl maleic, α-butyl maleic, α-phenyl maleic, fumaric, aconitic, α-chloromaleic, α-bromomaleic, and α-cyanomaleic acids including their salts, amides and esters. Anhydrides of the foregoing acids are also advantageously employed.

Co-monomers suitable for use with the above polycarboxylic acid monomers include α-olefins, such as ethylene, 2-methylpentene-1, propylene, isobutylene, 1- or 2-butene, 1-hexene, 1-octene, 1-decene, 1-dodecene, 1-octadecene, and other vinyl monomers, such as styrene, α-methyl styrene, vinyltoluene, vinyl acetate, vinyl chloride, vinyl formate, vinyl alkyl ethers, e.g. methylvinyl-ether, alkyl acrylates, alkyl methacrylates, acrylamides and alkylacrylamides, or mixtures of these monomers. Reactivity of some functional groups in the copolymers resulting from some of these monomers permits formation of other useful functional groups in the formed copolymer, including hydroxy, lactone, amine and lactam groups.

Any of the said carboxylic acids or derivatives may be copolymerized with any of the other monomers described above, and any other monomer which forms a copolymer with unsaturated carboxylic acids or derivatives. Although these copolymers can be prepared by direct polymerization of the various monomers, frequently they are more easily prepared by an after-reaction modification of an existing copolymer. Copolymers are conveniently identified in terms of their monomeric constituents. The names so applied refer to the molecular structure and are not limited to the polymers prepared by the copolymerization of the specified monomers.

Representative EMA-type carboxylic acid or anhydride-olefin polymers, especially maleic acid or anhydrideolefin polymers of the foregoing type are known, for example, from U.S. Pat. Nos. 2,378,629; 2,396,785; 3,157,595; and 3,340,680. Generally, the copolymers are prepared by reacting ethylene or other unsaturated monomer, or mixtures thereof, with the acid anhydride in the presence of a peroxide catalyst in an aliphatic or aromatic hydrocarbon solvent for the monomers but nonsolvent for the interpolymer formed. Suitable solvents include benzene, toluene, xylene, chlorinated benzene and the like. While benzoyl peroxide is usually the preferred catalyst, other peroxides such as acetyl peroxide, butyryl peroxide, dietertiary butyl peroxide, lauroyl peroxide and the like, or any of the numerous azo catalysts, are satisfactory since they are soluble in organic solvents. The copolymer preferably contains substantially equimolar quantities of the olefin residue and the anhydride residue. Generally, it will have a degree of polymerization of about 8 to 100,000, preferably about 100 to 5,000 and a molecular weight of about 1,000 to 1,000,000 preferably about 10,000 to 500,000. The properties of the polymer, such as molecular weight, for example, are regulated by suitable choice of the catalyst and control of one or more of the variables such as ratio of reactants, temperature, and catalyst concentration or the addition of regulating chain transfer agents, such as diisopropyl benzene, propionic acid, alkyl aldehydes, and the like. Numerous of these polymers are commercially available.

Following the formation of the initial EMA-type polymer, the polymer is preferably aggregated as described in the applicants' copending application Ser. No. 818,919, entitled "Aggregated Polyelectrolytes", filed July 25, 1977, now U.S. Pat. No. 4,118,554. This aggregation improves the filterability, drying characteristics and physical form of the polymer used in making the polyelectrolyte without significantly diminishing the protein adsorption capacity of the polyelectrolyte. However, said aggregation is not essential to the present invention.

The aforesaid initially prepared polymer, either aggregated or unaggregated, is cross-linked and substituted with the amine-imide groups in whatever sequence optimizes the properties being sought by tailoring the distribution of specific groups within the particles. These groups are essentially basic groups which can be aliphatic straight chain groups or can be alicyclic or aromatic groups. The aliphatic straight chain groups preferably are diloweralkylaminoloweralkylimide groups or loweralkyliminodi(loweralkylimide) linkages as described previously in U.S. Pat. Nos. 3,554,985 and 3,55,001. Such products are further illustrated by the general examples in the following section II:

II

The initial copolymers of anhydrides and another monomer can be converted to carboxyl-containing copolymers by reaction with water, and to ammonium, alkali and alkaline earth metal and alkylamine salts thereof by reaction with alkali metal compounds, alkaline earth metal compounds, amines or ammonia. Other suitable derivatives of the above polymers include the alkyl or other esters, alkyl amides, dialkyl amides, phenylalkyl amides or phenyl amides prepared by reacting carboxyl groups on the polymer chain with the selected amines or alkyl or phenylalkyl alcohol, as well as amino esters, amino amides, hydroxy amides and hydroxy esters, wherein the functional groups are separated by alkylene, phenyl, phenylalkyl, phenylalkylphenyl, or alkylphenylalkyl or other aryl groups. Moieties bearing amine or amine salts including quaternary salt groups are conveniently formed by reaction of the carboxyls of their anhydride precursors where applicable with polyfunctional amines such as dimethylaminopropylamine at higher temperatures forming an imide linkage with vicinal carboxyls. Such pendant free amine groups can then be converted, if desired, to their simple or quaternary salts.

Partial imides of a starting carboxyl or carboxylic acid anhydride containing polymer, e.g. EMA, are produced by:

(A) Heating a limiting amount of a secondary or tertiary aminoloweralkylamine with the anhydride or carboxyl-containing form of the polymer in a suitable solvent (e.g. xylene) at a temperature of about 140°–150° C. until water is no longer given off. Such a reaction simultaneously results in formation of imide groups in proportion to the amount of amine added and in the reformation of anhydride groups for the remainder of the polymer units. In this manner, imide-polymer products are formed which typically possess 2–100% imide linkages; however, these products generally are only partially substituted with the remaining unsubstituted carboxyl groups being in the free anhydride form.

(B) Alternatively, a partial amide polymer product can be converted to the partial imide polymer product by heating a partial amide-polymer product in vacuo at 140°–150° C. until water is no longer given off. Such an imide polymer product likwise possesses comparable proportions of imide and anhydride groups depending upon the number of amide groups originally contained in the starting partial amide-polymer product.

Partial secondary or tertiary aminoloweralkylamides of the starting carboxyl or carboxylic acid anhydride-containing polymer, e.g. EMA, are obtained by contacting the polymer with a limiting amount of the selected amine in suspension in a solvent such as benzene or hexane, resulting in formation of a partial amide-acid anhydride derivative of the polymer, or a corresponding amidecarboxylate derivative thereof. The number of amide groups is dependent upon the quantity of the amine used as compared with the quantity of polymer employed. Such amide-polymer products typically comprise 2–100% amide groups; however, these products generally are only partially substituted, with the remaining unsubstituted carboxyl groups being present as carboxyl or anhydride groups.

Suitable blocking and unblocking of the amine moiety of the reactant employed in preparing amines or imides may be effected when required. Residual, non-modified polymer units or anhydrides may optionally be converted to neutral groups or units by reaction with certain nonfunctional compounds including alkylamines, aminoalcohols and alcohols.

Alternatively, additional cationic character can be provided in the polymer through incorporation of monomers which impart a basic or cationic character such as C-vinyl pyridines, vinyl amine, the several aminosubstituted vinyl benzenes (or toluenes and the like), amine-bearing acrylates (or methacrylates and the like), vinyl imidazole and such similar monomers.

Thus, in any event, the polymer product will have residual active or reactive groups which can be of various types, including mixtures, but these residual active or reactive groups or residual "reactive sites" in the polymer will in one way or another comprise a certain percentage which are of a basic nature, so as to impart the requisite basic nature to the polymer product.

Especially preferred polymers subject to the previously referred to requirements are selected from the group consisting of ethylene/maleic acid or anhydride copolymers, styrene/maleic acid or anhydride copolymers, methylpentene/maleic acid or anhydride copolymers, and isobutylene/maleic acid or anhydride copolymers.

As will be apparent from the foregoing, the essential basic groups of the polycationic or polyampholytic polyelectrolyte (PE) employed are of an imide nature involving diloweralkylaminoloweralkylimide groupings, as produced by reacting a diloweralkylaminoloweralkylamine with the carboxyl groups of a pre-formed polymer or by polymerizing an unsaturated olefin with an unsaturated anhydride or acid having such pre-formed imide groups in at least a portion of the unsaturated polycarboxylic acid reactant. According to the invention, such groups are preferred for purposes of the invention.

Alternatively, whether such pre-formed groups are or are not present, imide groups can be provided by crosslinking the polymer with a loweralkyliminobis(-loweralkylamine) which in the process of crosslinking by reaction between the terminal amine groups of the crosslinker and carboxyl groups in the polymer chain is productive of imido groups at both ends of the crosslinking chain with formation of the desired loweralkyliminobis(loweralkylimide) linkages. Other groups, such as diloweralkylaminoloweralkylamine groups, from which the desired imide groups can be obtained by heating at elevated temperatures, can also be present. Also, diloweralkylaminoloweralkyl ester groups can be present, as well as other groups, so long as the prescribed percentages of imide groups of the prescribed type are also present in the polyelectrolyte molecule as well as the residual acid groups of the starting unsaturated acid or anhydride when the polyelectrolyte is a polyampholyte. As will be recognized, both the acid groups and the imide groups need not necessarily be present in the polyelectrolyte as such, but can be present in the form of their simple derivatives, e.g. salts, as already indicated.

The alicyclic or aromatic groups which can be substituted on the EMA-type polymers are for example, aminoloweralkyl-pyridine, piperidine, piperazine, picoline, pyrrolidine, morpholine and imidazole. These groups can be substituted on the polymer in a manner analogous to the aliphatic chain amines but by using, instead, cyclic amines such as, for example:
2-aminopyridine
2-amino-4-methylpyridine
2-amino-6-methylpyridine
2-(2-aminoethyl)-pyridine
4-(aminoethyl)-piperidine
3-amino-N-ethylpiperidine
N-(2-aminoethyl)-piperidine
N-(2-aminoethyl)-piperazine
3-picolylamine
4-picolylamine
2-(aminomethyl)-1-ethylpyrrolidine
N-(3-aminopropyl)-2-pyrrolidine
N-(2-aminoethyl)-morpholine
N-(3-aminopropyl)-morpholine
4-imidazole The carboxyl or anhydride blocking groups employed in the invention can be introduced in any desired sequence during the production of the aforesaid polyelectrolytes. However, they are preferably introduced after the crosslinking and substitution with the desired functional amine-imide group. Any remaining free carboxyl or anhydride groups will thus be blocked by employing an excess of the blocking agent.

Preferred carboxyl or anhydride blocking agents are alkoxyalkylamines having from about 2 to about 4 carbon atoms in the alkyl group and from about 1 to about 4 carbon atoms in the alkoxy group. The most preferred blocking agents are methoxypropylamine and methoxyethylamine. By way of comparison, anhydride-blocking agents such as hydroxypropylamine and hydroxyethylamine are ineffective for preventing the pre-activation of the coagulation factors fractionated with the polyelectrolytes.

The following specific examples will further illustrate the production and use of the polyelectrolyte polymers of this invention although it will be understood that the invention is not limited to these specific examples. The results obtained in several examples are set forth in convenient tabular form following the respective examples. In these examples, abbreviations of several materials are defined as follows:

MIBPA = methyl-imino-bis-propylamine
DMAPA = dimethylaminopropylamine
DEAEA - diethylaminoethylamine
HOEtA = monoethanolamine
HMDA = hexamethylenediamine

EXAMPLE 1

A 5-liter reaction flask, equipped with reflux condenser, Dean-Stark water take-off, stirrer, reagent addition vessel, thermometer and nitrogen-purge attachments, was charged with 193.05 g. ethylene/maleic anhydride copolymer (EMA) (1.5 moles, anhydride basis) and 2700 ml. xylene. The charge was stirred at 200 r.p.m. with a 6.5 inch blade-type stirrer while it was heated to the reflux temperature. This reflux temperature will vary from 135° to 139° C. depending on the water content of the EMA and upon whether this water was azeotropically removed during the ensuing reflux period. In this case the slurry was maintained at total reflux for 60 minutes under total reflux return at a temperature of 135° C. After 1 hour the reactor was cooled to 125° C. under nitrogen and 7.66 g. (0.075 mole) dimethylaminopropylamine (DMAPA) was added. Stirring was maintained for 1 hour at 125° C. without reflux after which 10.89 g. (0.075 mole) of methyliminobispropylamine (MIBPA) was added, following which the total mixture was stirred for an additional hour at 125° C. The mixture was heated to reflux (134° C.) and maintained at reflux for 7 hours while removing the water of reaction continuously by azeotropic distillation. The final temperature was 138° C. and 5.3 ml. of water was collected. The slurry temperature was lowered to 115° C. and 127.02 g. (1.42 moles) of methoxypropylamine (MOPA) was added. The mixture was stirred for 1 hour without reflux at 115°-118° C. and then the temperature was raised to 120° C. where refluxing of the xylene-water azeotrop began. Reflux was maintained for 6 hours while removing the water of reaction continuously by azeotropic distillation, final temperature was 138° C. and 23.6 ml. water was collected.

The product was recovered as the free amine form using the following procedure. The final slurry from above was filtered hot (100° C.) and the product cake was reslurried in 2700 ml. of a 3:1 mixture of xylene and ethanol, stirred at reflux temperature for one hour and filtered. This step was repeated a second time using a 3:1 xylene-alcohol extraction mixture. After again filtering, the product cake was reslurried in xylene (2700 ml.) and stirred 1 hour at reflux and filtered. The xylene extraction was repeated a second time and the final product cake was reslurried in 2700 ml. hexane for 1 hour at room temperature and filtered. The hexane extraction was repeated three additional times and the final filter cake air dried in a pan for 1 hour, screened through a 100 mesh seive without grinding and vacuum dried overnight at 50° C. There was obtained 165 g. of fine product (through 100 mesh) and 14 g. of coarse product (on 100 mesh). The fine product assayed for 8.09% nitrogen and was immediately and easily dispersable in 0.04 M. saline. The pH of such a dispersion (0.2 g. product in 20 ml. 0.04 M saline) was 8.10.

EXAMPLE 2

For work-up as the hydrochloride salt form, the final reaction slurry from Example 1 was filtered hot and the product cake reslurried at reflux in 3:1 xylene-alcohol two times, reslurried at reflux in xylene two times as in Example 1, and followed by two 1-hour room temperature extractions with 2700 ml. acetone. The filtered product was converted to the hydrochloride by reslurrying in 2700 ml. acetone and gradually adding with stirring (over 10 min.) 14 ml. conc. (12 N) hydrochloric acid and stirring at room temperature for two hours. The filtered product was subsequently washed (slurry with stirring) three consecutive times with 10 liters of water (deionized) for 2 hours each time and finally filtered. The filtered salt cake was reslurried four times in 2700 ml. acetone (1 hour each time) to remove the water, filtered, air dried for 30 minutes and vacuum oven dried at 55° C.

The final dried product was screened without grinding with 95% of the product going through a 100 mesh screen before bottling for use. The product analysed for 7.79% nitrogen and 2.62% chlorine as ionic chloride. 186 g. of salt form product (through 100 mesh) was obtained. It was dispersed in 0.04 M saline (5 g. per 120 ml.) and the dispersion had a pH of 3.85.

EXAMPLE 3

The procedure of Example 1 was repeated wherein the product composition was changed by adding different proportions of the amines employed in Example 1. The same amine reaction sequence was used as in Example 1 and in no case was any water added to the amines to facilitate reaction. All of the products were finished as the free amine derivatives as in Example 1. The initial 1-hour reflux period of EMA in xylene slurry was performed under total reflux as in Example 1 (no water removal) or as noted in the table with azeotropic reflux removing any water which may have been endogenous to the EMA.

| Run | Water Removed During Aggregation | DMAPA g. | mole % | MIBPA g. | mole % | MOPA g. | mole % | Product Total Yield g. | % N |
|---|---|---|---|---|---|---|---|---|---|
| 1 | No | 7.66 | 5.0 | 10.89 | 5.0 | 127.02 | 85 | 166 | 8.24 |
| 2 | No | 7.66 | 5.0 | 10.89 | 5.0 | 127.02 | 85 | 210 | 7.89 |
| 3 | No | 7.66 | 5.0 | 10.89 | 5.0 | 127.02 | 85 | 208 | 7.60 |
| 4 | No | 7.66 | 5.0 | 10.89 | 5.0 | 127.02 | 85 | 211 | 7.81 |
| 5 | No | 7.66 | 5.0 | 21.79 | 10.0 | 113.60 | 75 | 214 | 8.00 |
| 6 | No | 7.66 | 5.0 | 21.79 | 10.0 | 113.60 | 75 | 239 | 8.22 |
| 7 | Yes | 7.66 | 5.0 | 21.79 | 10.0 | 113.60 | 75 | 228 | 8.27 |
| 8* | Yes | 7.66 | 5.0 | 10.89 +10.89 | 5.0 5.0 | 113.60 | 75 | 237 | 8.05 |

-continued

| Run | Water Removed During Aggregation | DMAPA g. | DMAPA mole % | MIBPA g. | MIBPA mole % | MOPA g. | MOPA mole % | Product Total Yield g. | Product %N |
|---|---|---|---|---|---|---|---|---|---|
| 9 | No | 7.66 | 5.0 | 43.57 | 20.0 | 86.9 | 55 | 254 | 8.79 |
| 10 | Yes | 7.66 | 5.0 | 43.57 | 20.0 | 86.9 | 55 | 250 | 8.94 |
| 11 | Yes | 7.66 | 5.0 | 43.57 | 20.0 | 86.9 | 55 | 262 | 8.74 |

*In run 8 the MIBPA was added in two consecutive portions, each with a 1-hour reflux period, as a two-stage crosslinking variation before removing the water of reaction from DMAPA plus MIBPA.

EXAMPLE 4

When the initial 1-hour EMA-xylene reflux period is performed under conditions of azeotropic distillation, i.e. removing all water from these reactants before subsequent amine reactions, then the subsequent amine reactions are sluggish to start so that total reaction times are prolonged to accomplish complete reaction. Addition of small amounts of water with the various amines overcomes this difficulty. Several runs were made using the general method of Example 1 but with the EMA-xylene reflux water removed during the initial 1 hour period as in Example 3, Run No's 7, 8, 10 and 11. In these runs additional water was added variously with the three amines as indicated in the following table. All runs were finished as the free amine as in Example 1.

| Run | DMAPA mole % | DMAPA water added ml. | MIBPA mole % | MIBPA water added ml. | MOPA mole % | MOPA water added ml. | Product Total Yield g. | Product %N |
|---|---|---|---|---|---|---|---|---|
| 1 | 5 | None | 5 | 1.5 | 85 | None | 200 | 7.75 |
| 2 | 5 | None | 10 | 1.5 | 75 | None | 226 | 8.34 |
| 3 | 5 | None | 10 | 3.0 | 75 | 4.5 | 242 | 8.25 |
| 4 | 5 | 1.5 | 10 | None | 75 | 4.5 | 240 | 7.63 |
| 5 | 5 | None | 10 | 3.0 | 75 | None | 225 | 8.45 |
| 6 | 5 | None | 10 | 1.5 | 75 | None | 210 | 8.56 |
| 7* | 10 | None | 20 | 1.5 | 50 | 1.5 | 267 | 9.59 |
| | | | HMDA* | | | | | |
| 8** | 5 | None | 10 | 1.5 | 75 | None | 268 | 7.49 |
| 9** | 5 | None | 20 | 1.5 | 55 | None | 261 | 7.69 |

*MIBPA Added before DMAPA, all others in reverse order.
**HMDA=hexamethylenediamine used as crosslinker instead of MIBPA.

EXAMPLE 5

The equipment used in Example 1 was charged with 193.05 g. (1.5 mole) EMA and 2700 ml. xylene and the charge was brought to reflux (137° C.) with stirring at 200 rpm and refluxing was maintained for 1 hour during which time any water in the mixture was continuously removed by azeotropic distillation. A total of 1.6 ml. water was collected in the Dean Stark trap. After 1 hour the slurry was cooled to 125° C. and 7.66 g. (0.075 mole) DMAPA was added and this mixture was maintained for 1 hour at 125° C., after which a mixture of 21.70 g. (0.15 mole) MIBPA and 1.5 ml. water was added. After an additional hour at 125° C. the slurry was heated to reflux (136° C.) and maintained at reflux while continuously removing water in the Dean Stark trap for 15 hours, thereby removing a total of 6.3 ml. water at a final temperature of 138° C. The slurry was cooled to 120° C. and 113.65 g. (1.25 moles) MOPA was added and the resulting slurry held at 120° for an additional hour. The temperature was then raised to 136° C. and reflux with azeotropic removal of water continued for 6 hours to collect 21.5 ml. water. The product was converted to the hydrochloride salt following the procedure of Example 2. A total of four runs were made using varying amounts of concentrated hydrochloric acid (12 N) in order to test the effect of both deficient and excess HCl on the final product properties.

| Run | Conc. HCl Added ml. | % of Theory | Yield g. | pH of Saline Slurry | % N | % Cl | % Cl as ionic chloride |
|---|---|---|---|---|---|---|---|
| 1 | 8.0 | 0.5 | 206 | 6.95 | 8.24 | 1.77 | 1.70 |
| 2 | 15.0 | 1.0 | 207 | 5.55 | 8.10 | 3.00 | 2.76 |
| 3 | 30.0 | 2.0 | 214 | 4.40 | 8.22 | 3.32 | — |
| 4 | 60.0 | 4.0 | 219 | 4.10 | 8.21 | 3.40 | 3.37 |

EXAMPLE 6

The procedure of Example 5 was repeated except that after reaction of DMAPA and MIBPA there was added 95.77 g. (1.27 moles) methoxyethylamine(-MOEA) instead of the methoxypropylamine (MOPA). Two products were prepared, one as the free amine by the work-up procedures of Example 1 and the other as the HCl salt by the work-up procedure of Example 2.

| Run | Conc. HCl added, ml. | Yield g. | % N | % Cl |
|---|---|---|---|---|
| 1 | None | 206 | 8.61 | — |
| 2 | 15.0 | 205 | 8.15 | 3.18 |

EXAMPLE 7

The procedure of Example 1 was used to prepare products in which excess anhydride groups remaining after the reaction of DMAPA and MIBPA were totally reacted with either hydroxyethylamine, 3-hydroxypropylamine or 2-hydroxypropyl amine as shown in the following table. The products were prepared both as the free amine forms using the procedure in Example 1 and as the HCl salt using the procedure in Example 2. The initial hour aggregation period of EMA-xylene reflux was carried out under azeotropic removal of water and in each case the MIBPA was added as a mixture with 1.5 ml. water.

| | Product Composition(amine basis)* | | | | | |
|---|---|---|---|---|---|---|
| Run | mole % DMAPA | mole % MIBPA | mole % of finishing amine | | Product Form** | % N | % Cl |
| 1 | 5(7.66g) | 5(10.89g) | 85(87.05g) | Ethanolamine | F.A. | 8.57 | — |
| 2 | 5 | 5 | 85(87.05g) | Ethanolamine | HCl | 8.41 | 1.81 |
| 3 | 5 | 5 | 85(107g) | 3-hydroxypropylamine | F.A. | 8.02 | — |
| 4 | 5 | 5 | 85(107g) | 3-hydroxypropylamine | HCl | 7.65 | 1.82 |
| 5 | 5 | 5 | 85(113g) | 2-hydroxypropylamine | F.A. | 7.93 | — |
| 6 | 5 | 5 | 85(113g) | 2-hydroxypropylamine | HCl | 7.75 | 1.85 |
| 7 | 5 | 7(15.25g) | 81(85.2g) | Ethanolamine | F.A. | 8.63 | — |
| 8 | 5 | 7 | 81(85.2g) | Ethanolamine | HCl | 8.49 | 2.57 |

*All composition mole ratios in this and succeeding examples are on an amine basis. Since the cross-linking agent reacts at both ends, the moles of cross-linking agent would be double that shown when the mole ratio is converted to an anhydride basis.
**Finished as F.A. = Free Amine; HCl = hydrochloride salt

EXAMPLE 8

A series of polyelectrolytes were prepared in which the crosslinker (MIBPA) was maintained at 5 mole % and the blocking amine to react with excess anhydride groups was always ethanolamine at the 85 mole % level. The functional moiety, that which provided potential cationic function, was maintained at 5 mole % but the nature and structure of the functional moiety was altered by use of sixteen different reactive amines as set forth in the following table. A general procedure was used as follows:

All preparations utilized the same equipment and the same EMA and xylene charge as in Example 1. The slurry was heated to 90°–95° C. and 10.89 g. (0.075 mole) MIBPA was added and stirred at 95° C. for 1 hour. Then 0.075 mole of the functional amine (see table below) was added and stirred at 95° C. for 1 hour. The slurry was heated to reflux (134° C.) and water of reaction was completely removed by azeotropic distillation to a final temperature of 139° C. The slurry was then cooled to 95° C. and 87.05 g. of hydroxyethylamine was added and the slurry stirred at 95° C. for 1 hour. The slurry temperature was then raised to 134° C. and the total water of reaction was completely removed by azeotropic distillation to a final temperature of 139° to 140° C. The final slurry was filtered hot and worked up as the free amine by the procedure of Example 1, dried, ground by ball milling and screened through a 100 mesh screen.

TABLE EXAMPLE 8

| Run No. | Functional amine used | Grams amine used | Product yield g. | N % |
|---|---|---|---|---|
| 1 | Dimethylaminoethylamine | 6.60 | 240 | 8.86 |
| 2 | Diethylaminoethylamine | 8.71 | 255 | 8.68 |
| 3 | Dimethylaminopropylamine | 7.66 | 252 | 8.71 |
| 4 | Diethylaminopropylamine | 9.84 | 228 | 8.61 |
| 5 | Dihydroxyethylaminopropylamine | 12.20 | 256 | 8.56 |

TABLE EXAMPLE 8-continued

| Run | Functional amine used | Grams amine used | Product yield g. | N % |
|---|---|---|---|---|
| 6 | Dibutylaminopropylamine | 13.98 | 255 | 8.58 |
| 7 | 2-amino-5-diethylamino pentane | 11.86 | 240 | 8.63 |
| 8 | 2-aminomethyl-1-ethyl-pyrrolidine | 9.61 | 237 | 7.50 |
| 9 | 3-amino-N-ethyl piperidine | 9.61 | 232 | 8.67 |
| 10 | N-2-aminoethyl piperidine | 9.61 | 219 | 8.73 |
| 11 | N-3-aminopropyl-2-pyrrolidone | 10.66 | 221 | 8.35 |
| 12 | N-2-aminoethyl morpholine | 10.06 | 250 | 8.75 |
| 13 | N-3-aminopropyl morpholine | 10.81 | 252 | 8.78 |
| 14 | N-2-aminoethyl piperazine | 9.69 | 240 | 9.13 |
| 15 | 2(2-aminoethyl)pyridine | 9.64 | 240 | 8.97 |
| 16 | N-phenylethylenediamine | 10.21 | 249 | 8.91 |

In the above series, the amines in runs 1 through 7 are examples of dialkylaminoalkylimide substitution on the polyelectrolyte while those in runs 8 through 15 are examples of heterocyclic aminoalkylimide substitution. Three of the above were also then prepared as preformed hydrochloride salts for evaluation. The preparative method of Example 1 was followed and the conversion to the salt followed the procedure in Example 2. The dimethylaminopropylamine (run 3 above) was selected as representative of the dialkylaminoalkylimide substitution and the 3-amino-N-ethyl piperidine and N-3-aminopropyl morpholine (runs 9 and 13 above) were selected as representative of the heterocyclic aminoalkylimide substitution. In all three cases, polyelectrolytes in the salt form were prepared using both hydroxyethylamine and methoxypropylamine as the third amine to react with all excess anhydride groups. These run preparations are given in Example 9.

EXAMPLE 9

The methodology of Examples 1 and 2 were used to prepare preformed hydrochloride salts of polyelectrolytes having the general composition of 5 mole % crosslink as MIBPA, 5 mole % of three different functional aminoalkylimide moieties and 85 mole % of non-functional imide moieties as shown in the table below.

| | Composition, mole % | | | Product yield g. | % N | % Cl |
|---|---|---|---|---|---|---|
| Run | MIBPA | Functional Amine | Third Amine | | | |
| 1 | 5 | 5 - Dimethylaminopropyl amine | 85 - Hydroxyethyl amine | 236 | 8.41 | 1.81 |
| 2 | 5 | 5 - Dimethylaminopropyl amine | 85 - Methoxypropyl amine | 186 | 7.79 | 2.62 |
| 3 | 5 | 5 - 3-amino-N-ethyl piperidine | 85 - Hydroxyethyl amine | 238 | 7.37 | 1.54 |

| | Composition, mole % | | Product yield | % | % |
|---|---|---|---|---|---|
| Run | MIBPA | Functional Amine | Third Amine | g. | N | Cl |
| 4 | 5 | 5 - 3-amino-N-ethyl piperidine | 85 - Methoxypropyl amine | 244 | 8.19 | 1.20 |
| 5 | 5 | 5 - 3-aminopropyl morpholine | 85 - Hydroxyethyl amine | 250 | 8.55 | 1.68 |
| 6 | 5 | 5 - 3-aminopropyl morpholine | 85 - Methoxypropyl amine | 234 | 7.58 | 1.59 |

EXAMPLE 10

This example illustrates the preparation of methoxypropylimide derivatives of styrene-maleic anhydride copolymer following the procedure of Example 5. Equipment utilized was the same as in Example 1. The initial charge of 101.1 g. (0.5 mole) styrene-maleic anhydride and 2.7 liters xylene was refluxed at 135° C. with azeotropic distillation of water for 1 hour and then cooled to 125° C. whereupon 2.55 g. (0.025 mole) DMAPA was added and the mixture heated without reflux for 1 hour. After 1 hour a mixture of 2.91 g. (0.025 mole) hexamethylene diamine (HMDA) and 1.0 ml. water was added and heating without reflux was continued for one hour. After 1 hour a second addition of 2.55 g. DMAPA (0.025 mole) was made followed by a 1 hour heating period at 125° C. The slurry was then heated to 135° C. and refluxed 4 hours under azeotropic distillation of water (1.25 ml. collected). After cooling to 125° C., 40.56 g. methoxypropylamine was added and the slurry heated at 125° C. for 1 hour. The slurry was then heated to reflux (136° C.) under azeotropic distillation for 6 hours thereby removing 8.2 ml. water in the Dean Stark trap. The final temperature was 138° C. The product was obtained as the hydrochloride salt using the procedure of Example 2 employing 5.0 ml. concentrated (12 N) hydrochloric acid. The final washed and dried product collected was 113.0 g. and analysed 5.27% nitrogen and 1.00% chlorine.

EXAMPLE 11

This example illustrates the preparation of methoxypropylimide derivatives of isobutylenemaleic anhydride copolymer following the procedure of Example 5 and using the equipment of Example 1. The initial charge of 154.16 g. (1.0 mole) of isobutylene-maleic anhydride and 2.7 liters xylene was refluxed at 135° C. under azeotropic removal of water for 1 hour and then cooled to 125° C. 5.11 g. (0.05 mole) DMAPA was then added and the slurry was heated at 120°-125° C. without refluxing for 1 hour. To this slurry 7.26 g. (0.05 mole) MIBPA and 1.0 ml. water was added and again the mixture was heated for 1 hour at 120°-125° C. without refluxing. The slurry was then heated to reflux (135° C.) and water removed by azeotropic distillation over a period of 4 hours. The final temperature was 137° C. and 1.20 ml. water was collected. After lowering the slurry temperature to 120° C. there was added 84.7 g. methoxypropylamine and this mixture was heated at 120°-125° C. without reflux for 1 hour. The slurry temperature was raised to reflux (135° C.) and water of reaction was azeotropically removed over a 6 hour period. The final temperature was 137° C. and 16.3 ml. water was obtained. The product was obtained as the hydrochloride salt using the procedure of Example 2 employing 10.0 ml. concentrated (12 N) hydrochloric acid. The final washed and dried product collected was 186 g. and analysed 6.44% nitrogen and 1.25% chlorine.

EXAMPLE 12

A 5-liter reaction flask, equipped with reflux condenser, Dean-Stark water take-off, stirrer, reagent addition vessel, thermometer and nitrogen-purge attachments, was charged with 193.05 g. ethylene/maleic anhydride copolymer (EMA) (1.5 moles, anhydride basis) and 2700 ml. xylene. The charge was stirred at 200 r.p.m. with a 6.5 inch blade-type stirrer while it was heated to the reflux temperature. The slurry was maintained at total reflux for 60 minutes under total reflux return at a temperature of 135° C. After 1 hour the reactor was cooled to 125° C. under nitrogen and a solution mixture of 10.89 g. MIBPA (0.075 mole) and 1.5 ml. water was added. The mixture was heated to reflux (134° C.) and maintained at reflux for 1 hour while continuously removing water azeotrope (final temperature was 137° C.). The reaction mixture was again lowered to 125° C. under nitrogen and a solution mixture of 153.3 g. DMAPA (1.5 moles) and 4.5 ml. water was added. The slurry was then heated to 133° C. and held at this temperature (1-10 min.) until refluxing began as a consequence of water being formed during the chemical reaction. Stirring and refluxing of the reacting slurry was continued until water removed by azeotropic distillation was complete. The final temperature was 139° C.

For work-up as the hydrochloride salt form, the above slurry was filtered hot and the product cake was reslurried in 2700 ml. of a 3:1 mixture of xylene and alcohol, stirred at reflux temperature for one hour and then filtered hot. This was repeated a second time for a two hour period and a third time for a three hour refluxing period, in each case followed by hot filtration. The resulting extracted product was reslurried in 2700 ml. acetone for 1 hour at room temperature and filtered and the cake was again slurried in 2700 ml. acetone for 1 hour at room temperature and filtered. This extracted cake was slurried in 2700 ml. alcohol at room temperature and converted to the hydrochloride salt by adding over a period of 10 minutes 112 ml. of concentrated (12 N) hydrochloric acid and stirring at room temperature for 2 hours. The filtered product was subsequently washed (slurry with stirring) three consecutive times with 10 liters of deionized water for 2 hours each time and filtered. The salt form cake was reslurried 4 times in 2700 ml. acetone (1 hour each time) to remove the water, filtered, air dried for 30 minutes and vacuum oven dried at 55° C. overnight. The final product consisted of 333 g. screened through 100 mesh (not ballmilled or ground) with an analysis of 10.65% Nitrogen and 13.03% chlorine as chloride ion.

EXAMPLE 13

Using the same equipment and essentially the same procedure as in Example 1, a sample of polyelectrolyte was prepared containing only MIBPA crosslinker and MOPA (methoxypropylimide) moieties, i.e. no DMAPA or other functional amines.

The charge of 193.05 g. of EMA and 2700 ml. xylene was refluxed 1 hour under water takeoff at 135° C. removing 1.2 ml. water. This slurry was cooled to 125° C. and 13.37 g. (0.150 mole) MOPA was added and stirred at 125° C. for 1 hour. Then the MIBPA was added in two stages, first by adding 21.79 g. MIBPA (0.150 mole) plus 1.5 ml. water and stirring for 1 hour without reflux at 125° C. followed by raising the temperature to 135° C. and taking off water by azeotroping under reflux for 4 hours, thereby removing 7.4 ml. water. After cooling to 125° C. a second addition of 21.79 g. MIBPA (0.150 mole) plus 1.5 ml. water was made and the slurry heated at 125° C. for 1 hr. without refluxing. A second azeotropic reflux water removal was then carried out at 138° C., thereby removing 5.7 ml. water over 7 hours. The slurry was again cooled to 125° C. and 80.23 g. MOPA was added, stirred at 125° C. for 1 hour and then azeotropically refluxed (135° C. to 138° C.) for 8 hours, thereby removing 16.2 ml. water. The final slurry was filtered hot and finished as the free amine using the procedure of Example 1. The product consisted of 260 g. with a Nitrogen content of 8.57%.

EXAMPLE 14

This example illustrates the methods used for adsorbing Factor VIII clotting factor from human plasma to various polyelectrolytes described in Examples 1 through 13, eluting and recovering the Factor VIII from the polymer—Factor VIII complex for assay of (1) recovery or yield of Factor VIII, and (2) content of activating enzymes which influence (shorten) the clotting time properties of the Factor VIII. The methods of assay are given in Example 15.

The human plasma used for fractionation studies was fresh frozen plasma from whole blood donations, obtained from the St. Louis Red Cross. The total protein content of such plasma varied from 60 to 80 grams per liter, higher concentrations being observed in the summer than in the winter. The units received were either O positive or A positive in type.

Although not absolutely necessary, clotting Factor IX was removed from the plasma as an initial step prior to adsorbing Factor VIII. The following steps describe the over all process.

1. Thaw 5 units of fresh frozen plasma in a 37° C. water bath.
2. Pool the thawed plasma in a polyethylene or polypropylene beaker. Measure 1 liter into a polyethylene graduated cylinder and pour into a 2-liter polyethylene beaker.
3. Add 0.35 to 0.50 grams of polyelectrolyte from Example 12, and adjust the pH to 8.0 with 1.0 molar NaOH on a magnetic stirrer. Stir 20 minutes maintaining the pH at 8.0.
4. Filter on a 12.5 cm. Buchner funnel with Whatman No. 54 paper into a polyethylene bottle inside a 4 liter bottomless vacuum flask on a glass plate. Save the filtrate.
5. Scrape the filtered polymer from the filter paper into a 100 ml. polyethylene beaker, wash the filter paper with 20 ml. distilled water and add to the polymer in the beaker. Stir 5 minutes on a magnetic stirrer. Filter through a Whatman No. 1 paper in a 4.25 cm. Buchner funnel as before into a polyethylene beaker.
6. Combine the filtrates from steps 4 and 5 as Factor IX deficient plasma from which the Factor VIII can be removed in the following steps.

For screening purposes 10 ml. aliquots of this Factor IX deficient plasma were used in the following Factor VIII fractionation procedure. With proper equipment modifications the same general procedure was used to remove Factor VIII from 1-liter portions of Factor IX deficient undiluted plasma.

7. Disperse 0.50 grams of the polyelectrolyte to be used in 10 ml. of 0.154 M. saline and adjust the pH to 4.0 with either 1.0 N HCl or 1.0 M citric acid. Citric acid generally is preferred because of its stabilizing effect on Factor VIII. If the amine form of the polyelectrolyte is used the pH is adjusted with either HCl or citric acid, however if the preformed HCl salt form is used the pH will be close to 4.0 upon dispersion. All of the following operations using this 10 ml. size aliquot were done in 50 ml. polypropylene or polycarbonate centrifuge tubes. Stirring was done with very small magnetic bars.
8. Centrifuge the dispersion from Step 7 for 5 min. at 2000 r.p.m. and discard the supernate.
9. Add 10 ml. of 0.154 M saline and carefully adjust the pH to 5.8 with either 1.0 or 0.1 N NaOH.
10. Centrifuge the dispersion from Step 9 for 5 min. at 2000 r.p.m. and discard the supernate.
11. Carefully adjust the Factor IX deficient plasma from Step 6 to 5.8 with 1.0 M citric acid.
12. Add a 10 ml. aliquot of the plasma from Step 11 to the sedimented polyelectrolyte from Step 10. Stir for 20 minutes maintaining the pH at 5.8.
13. Centrifuge for 5 min. at 2000 r.p.m.
14. Remove a proper sample of supernate from Step 13 for Factor VIII (non-adsorbed) assays (See assay methods in Example 15). Discard the rest of the supernate.
15. Add 10 ml. of 0.154 M saline to the polymer-Factor VIII complex from Step 13, stir 5 min., centrifuge and discard the supernate.
16. Add 10 ml. of 1.7 M saline to the polymer-Factor VIII complex from Step 15 and adjust the pH to 6.0 with 0.10 M citric acid to elute the Factor VIII.
17. Stir for 20 minutes keeping the pH at 6.0.
18. Centrifuge 5 min. at 2000 r.p.m. and remove a proper sample of the supernate for Factor VIII (recovered) assays. Discard the remaining supernate.

With proper equipment modifications to filtration-type operation and using minor modifications in washing and elution methods the above method was used for 1-liter size fractionations of Factor VIII, from Step 6, using 60 g. of polyelectrolyte per liter of plasma. Again, assay for Factor VIII was performed on Step 14 filtrate (non-adsorbed Factor VIII) and on Step 18 filtrate for Factor VIII recovery.

EXAMPLE 15

Two evaluations were used to compare the resins previously described with respect to (1) recovery (comparative yield) of Factor VIII (AHF) from undiluted human plasma by the methodology of Example 14 and (2) the comparative level of activation of the Factor VIII so obtained.

(1) Recovery or yield of Factor VIII

A two-stage assay for measurement of AHF was used as a modification of the thromboplastin generation test as described by R. J. Biggs and A. S. Douglas, "The Thromboplastin Generation Test (TGT", *J. Clin. Pathol.* 1, 15–22 (1953). Essentially, this test measures the time to clot a standard substrate plasma (fresh-platelet-poor) after generation of an intermediate level of clotting activity by the time controlled addition of required clotting factors from other sources. The factors required for normal TGT in vitro clotting times (12–20 sec.) are Factors XII, XI, IX, VIII, V, phospholipid and $CaCl_2$. These factors are provided by the initial charges of $CaCl_2$, human serum for Factors XII, XI and IX, bovine serum for Factor V and a chloroform human brain extract for phospholipid on a time schedule followed by addition of platelet poor substrate plasma. The time of clotting of the final substrate plasma is measured automatically. Fresh plasma control (same plasma used for Factor VIII fractionation) or final AHF eluents, at proper dilution, are added as the measurable Factor VIII source before the final addition of substrate plasma.

Standard curves were prepared using a plasma of known AHF content standardized against a Squibb preparation distributed through the Bureau of Biologics which contained 1 unit of AHF per ml. The standard curves plotted clotting time in seconds against units of AHF activity per ml. (dilutions of above plasma control) on log-log paper. AHF content in units/ml. for test samples were obtained from these standard curves. Standard curves were prepared for each days run of AHF determinations.

The entire assay was time and temperature controlled using a BBL Fibrometer "Fibro System$^{TM}$", distributed by the BBL Division of Becton, Dickinson and Co., Cockeysville Maryland, equipped with two Thermal Prep Block heating units and a time controlling automatic pipette.

(2) AHF Activation Assay

The assay was designed to measure relative activation times of AHF (Factor VIII) outside the plasma environment as a modification of the above partial thromboplastin time test. In this test only phospholipid and $CaCl_2$ were added to the platelet poor plasma substrate. Clotting times were measured on the BBL Fibrometer by adding proper test AHF dilutions to the plasma substrate. A non-activated plasma control in this test consistently gave clotting times of over 190 seconds. Faster clotting times below 150 seconds are indicative of activation or the presence of activating enzymes. Two controls of fast clotting time preparations as well as a plasma and blank buffer control were run with each series of activation determinations.

Recovery assays were run on supernates from Steps 14 and 18 of Example 14 while activation assays were run on Step 18 supernates. All supernates were properly diluted in imidazole buffer to give final saline levels below 0.08 Molar.

EXAMPLE 16

AHF yield and Activation of materials prepared by Examples using 10 ml. Plasma Fractionation of Example 14.

The wide variety of materials prepared by Examples 1 through 13 were evaluated for Factor VIII fractionation and activation by the procedure in Example 14 and assayed for these parameters by Example 15 assays. The results given below are for fractionations using 10 ml. plasma and using from 0.1 to 0.8 g. PE per 10 ml. plasma. Pre-pHing, for PEs prepared and used as the amine form (see Step 7, Example 14) formed the "in situ" salt during the fractionation procedure and was done either with HCl or citric acid as noted.

The plasma, as indicated in Example 14, varied from batch-to-batch, and winter to summer in total protein content. Likewise the various units of plasma used for these studies varied in AHF (Factor VIII) content from 0.8 to 1.3 units per ml. as assayed under Example 15—Assay—1. The clotting time of the plasma, using the activation test (Example 15—Assay-2) varied between 185 and 240 seconds.

In the following table:
FA = Free Amine
HCl = HCl salt form

TABLE EXAMPLE 16

| Polyelectrolyte composition from Example No. | Form Used | g. PE per 10 ml. Plasma | Pre-pHed with | Recovery AHF(VIII) units/ml | AHF Activation Clotting Times sec. | Activation |
|---|---|---|---|---|---|---|
| 1 | FA | 0.6 | citric | 0.72 | 299 | No |
| 1 | FA | 0.4 | HCl | 0.56 | 270 | No |
| 1 | FA | 0.4 | No* | 0.62 | 273 | No |
| 2 | HCl | 0.8 | No | 0.49 | 259 | No |
| 2 | HCl | 0.5 | No | 0.42 | 272 | No |
| 7 Run 2 | HCl | 0.4 | No | 0.43 | 104 | Yes |
| " | HCl | 0.5 | No | 0.66 | 113 | Yes |
| " | HCl | 0.4 | No | 0.53 | 98 | Yes |
| 3 Run 1 | FA | 0.5 | citric | 0.49 | 198 | No |
| -2 | FA | 0.4 | HCl | 0.56 | 270 | No |
| -3 | FA | 0.6 | citric | 0.65 | 308 | No |
| -4 | FA | 0.6 | citric | 0.50 | 324 | No |
| -5 | FA | 0.6 | citric | 0.90 | 317 | No |
| -6 | FA | Not Tested | — | — | — | — |
| -7 | FA | 0.6 | citric | 0.60 | 340 | No |
| -8 | FA | 0.5 | citric | 0.78 | 269 | No |
| -9 | FA | 0.6 | citric | 0.80 | 317 | No |
| -10 | FA | Not Tested | — | — | — | — |
| -11 | FA | Not Tested | — | — | — | — |
| 4 Run 1 | FA | Not Tested | — | — | — | — |
| -2 | FA | 0.5 | HCl | 0.56 | 269 | No |
| -3 | FA | 0.5 | citric | 0.67 | 283 | No |
| -4 | FA | 0.5 | citric | 0.57 | 305 | No |

TABLE EXAMPLE 16-continued

| Polyelectrolyte composition from Example No. | Form Used | g. PE per 10 ml. Plasma | Pre-pHed with | Recovery AHF(VIII) units/ml | AHF Activation Clotting Times sec. | Activation |
|---|---|---|---|---|---|---|
| -5 | FA | 0.5 | citric | 0.72 | 303 | No |
| -6 | FA | 0.5 | citric | 0.61 | 315 | No |
| -7 | FA | 0.4 | HCl | 0.49 | 296 | No |
| -8 | FA | 0.5 | citric | 0.57 | 277 | No |
| -9 | FA | 0.5 | citric | 0.64 | 314 | No |
| 5 Run 1 | HCl | 0.5 | No | 0.76 | 258 | No |
| 2 | HCl | 0.5 | No | 0.72 | 254 | No |
| 3 | HCl | 0.5 | No | 0.80 | 261 | No |
| 4 | HCl | 0.5 | No | 0.80 | 338 | No |
| 7 Run 2 | HCl | 0.5 | No | 0.62 | 111 | Yes |
| 6 Run 1 | FA | 0.5 | citric | 0.61 | 252 | No |
| 2 | HCl | 0.5 | No | 0.58 | 240 | No |
| 7 Run 1 | FA | 0.5 | citric | 0.43 | 198 | No |
| 2 | HCl | 0.5 | No | 0.57 | 107 | Yes |
| 3 | FA | 0.5 | citric | 0.55 | 225 | No |
| 4 | HCl | 0.5 | No | 0.60 | 91 | Yes |
| 5 | FA | 0.5 | citric | 0.49 | 248 | No |
| 6 | HCl | 0.5 | No | 0.57 | 94 | Yes |
| 7 | FA | 0.5 | HCl | 0.45 | 231 | No |
| 8 | HCl | 0.5 | No | 0.51 | 117 | Yes |
| Ex. 8 Run 1 | FA | 0.5 | citric | 0.45 | 299 | No |
| 2 | FA | Not Tested | — | — | — | — |
| 3 | FA | 0.5 | citric | 0.54 | 272 | No |
| 4 | FA | 0.5 | citric | 0.64 | 279 | No |
| 5 | FA | 0.5 | citric | 0.59 | 244 | No |
| 6 | FA | Not Tested | — | — | — | — |
| 7 | FA | Not Tested | — | — | — | — |
| 8 | FA | Not Tested | — | — | — | — |
| 9 | FA | 0.5 | HCl | 0.43 | 252 | No |
| 10 | FA | 0.5 | citric | 0.66 | 314 | No |
| 11 | FA | 0.5 | citric | 0.42 | 257 | No |
| 12 | FA | 0.5 | citric | 0.62 | 246 | No |
| 13 | FA | 0.5 | citric | 0.52 | 279 | No |
| 14 | FA | 0.5 | citric | 0.42 | 257 | No |
| 15 | FA | 0.5 | citric | 0.57 | 253 | No |
| 16 | FA | 0.5 | citric | 0.48 | 288 | No |
| Ex.9 Run 1 | HCl | 0.5 | No | 0.66 | 113 | Yes |
| 2 | HCl | 0.5 | No | 0.42 | 272 | No |
| 3 | HCl | 0.5 | No | 0.58 | 90 | Yes |
| 4 | HCl | 0.5 | No | 0.54 | 225 | No |
| 5 | HCl | 0.5 | No | 0.55 | 146 | Yes |
| 6 | HCl | 0.5 | No | 0.50 | 218 | No |
| 10 | HCl | 0.5 | No | 0.39 | 172 | No |
| 11 | HCl | 0.5 | No | 0.33 | 210 | No |
| 12 | HCl | 0.4 | No | 0.30 | 253 | No |
|  | HCl | 0.1 | No | 0.54 | 205 | No |
| 13 | FA | 0.5 | HCl | 0.52 | 263 | No |

*pH adjusted directly to 5.8 with citric acid. Was not pre-pHed to 4.0.

EXAMPLE 17

Several polyelectrolytes prepared with methoxypropyl amine and described in the previous Examples 1 through 13 were used to fractionate the Factor VIII from liter size plasma pools using the procedure described in Example 14 but with proper modifications in equipment and reagent amounts necessary to accomodate the larger size operation.

EXAMPLE 18

Two samples of AHF (Factor VIII) prepared using polyelectrolytes from Example 1 and Example 7 run 2 were compared for toxic manifestations by I.V. injection into beagle dogs. Dogs of 8–9 kg. weight were used and the AHF was prepared in sterile water at 10 units per ml. Single doses of 100 units (10 ml.) were given to each dog. The following results were noted.

| Polyelectrolyte composition from Example | Form Used | g. PE per liter plasma | pre-pHed with | Recovery AHF(VIII) units per liter plasma | AHF Activation Clotting Time seconds | Activation |
|---|---|---|---|---|---|---|
| 12 | HCl | 10 | No | 223 | 210 | No |
| 1 | FA | 60 | citric | 600 | 287 | No |
| 3 Run 3 | FA | 60 | citric | 406 | 301 | No |
| 4 Run 1 | FA | 60 | citric | 737 | 300 | No |
| 3 Run 5 | FA | 60 | citric | 650 | 265 | No |
| 3 Run 7 | FA | 60 | citric | 510 | 364 | No |
| 4 Run 2 | FA | 60 | citric | 770 | 336 | No |
| 3 Run 9 | FA | 60 | citric | 480 | 239 | No |

| Dog | 1 | 2 |
| --- | --- | --- |
| Polyelectrolyte from: | Example 1 | Example 7 run 2 |
| Behavior after injection: | Normal | Rotated in cage (CNS disturbance) |
| Blood Pressure[1] | Normal | Raised |
| Hematocrit | Normal (1–24 hr) | Lowered substantially |
| Platelet count[3] | No change (1–24 hr) | Lowered 60% |
| Pulse[1] | Normal | — |
| White Cells[2] | No change (1–24 hr) | — |
| Red Cells[2] | No change (1–24 hr) | — |
| Hemoglobin | No change (1–24 hr) | — |
| Blood Chemistry[4] | Normal (1–24 hr) | — |

[1]Via femoral cathetor connected to a recording physiograph for blood pressure and pulse.
[2]Via a Coulter counter
[3]Via a Hemocytometer
[4]Run on a Technicon SMAC system (18 assays).

The above results show a total lack of toxic effects for the polyelectrolyte derived Factor VIII using Example 1 which employed methoxypropylamine in distinct contrast to several severe toxic effects with Factor VIII derived from polyelectrolyte using Example 7 run 2 which employed hydroxyethylamine and was preformed as the hydrochloride salt.

What is claimed is:

1. A method for separating specific blood coagulation factor from admixture with other blood proteins in a fluid medium comprising the step of contacting said medium with a water-insoluble, cross-linked polyelectrolyte copolymer of (a) unsaturated monomer having from 2 to about 18 carbon atoms and (b) a monomer selected from the group consisting of unsaturated polycarboxylic acid or anhydride having from about 4 to about 12 carbon atoms which is partially substituted at its free carboxyl or anhydride sites with amine-imides and which is further characterized in that substantially all the remaining free carboxyl or anhydride sites are blocked with alkoxyalkylamine, to thereby selectively adsorb said specific coagulation factor to the substantial exclusion of said other blood proteins without producing any substantial preactivation of said specific coagulation factor.

2. The method of claim 1 in which the copolymer is a copolymer of maleic acid or anhydride and monomer selected from the group consisting of ethylene, styrene and isobutylene.

3. The method of claim 2 in which the copolymer is a copolymer of ethylene and maleic acid or anhydride.

4. The method of claim 1 in which the amine-imide is selected from the group consisting of diloweralkylaminoloweralkylimide and loweralkyliminodi(loweralkylimide).

5. The method of claim 1 in which the copolymer is cross-linked with methyliminobispropylamine and the amine-imide is dimethylaminopropylimide.

6. The method of claim 1 in which the alkoxyalkylamine is selected from the group consisting of methoxyethylamine and methoxypropylamine.

7. The method of claim 1 in which the partial substitution with amine-imide ranges from about 2% to about 90% of the free carboxyl or anhydride sites.

8. The method of claim 1 in which the specific coagulation factor is Factor VIII and the contacting with the polyelectrolyte is carried out at a pH ranging from about 5.5 to about 9.5.

9. In the method of making a water-insoluble, cross-linked polyelectrolyte of the type suitable for the factionation of blood components and comprising a copolymer of (a) unsaturated monomer having from 2 to about 18 carbon atoms and (b) a monomer selected from the group consisting of unsaturated polycarboxylic acid or anhydride having from about 4 to about 12 carbon atoms which is partially substituted at its free carboxyl or anhydride sites with amine-imides, the improvement comprising blocking substantially all the remaining free carboxyl or anhydride sites with alkoxyalkylamine whereby said polyelectrolyte can be used for the separation of specific blood coagulation factor from other blood proteins in a fluid medium without thereby causing any substantial preactivation of said specific coagulation factor.

10. The method of claim 9 in which the copolymer is a copolymer of maleic acid or anhydride and monomer selected from the group consisting of ethylene, styrene and isobutylene.

11. The method of claim 10 in which the copolymer is a copolymer of ethylene and maleic acid or anhydride.

12. The method of claim 9 in which the amine-imide is selected from the group consisting of diloweralkylaminoloweralkylimide and loweralkyliminodi(loweralkylimide).

13. The method of claim 9 in which the copolymer is cross-linked with methyliminobispropylamine and the amine-imide is dimethylaminopropylimide.

14. The method of claim 9 in which the alkoxyalkylamine is selected from the group consisting of methoxyethylamine and methoxypropylamine.

15. The method of claim 9 in which the partial substitution with amine-imide ranges from about 2% to about 90% of the free carboxyl or anhydride sites.

16. A water-insoluble, cross-linked polyelectrolyte of the type suitable for the fractionation of blood components comprising a copolymer of (a) unsaturated monomer having from 2 to about 18 carbon atoms and (b) a monomer selected from the group consisting of unsaturated polycarboxylic acid or anhydride having from about 4 to about 12 carbon atoms which is partially substituted at its free carboxyl or anhydride sites with amine-imides, and which is further characterized in that substantially all the remaining free carboxyl or anhydride sites are blocked with alkoxyalkylamine whereby said polyelectrolyte can be used for the separation of specific blood coagulation factor from other blood proteins in a fluid medium without thereby causing any substantial pre-activation of said specific coagulation factor.

17. The polyelectrolyte of claim 16 in which the copolymer is a copolymer of maleic acid or anhydride and monomer selected from the group consisting of ethylene, styrene and isobutylene.

18. The polyelectrolyte of claim 17 in which the copolymer is a copolymer of ethylene and maleic acid or anhydride.

19. The polyelectrolyte of claim 16 in which the amine-imide is selected from the group consisting of diloweralkylaminoloweralkylimide and loweralkyliminodi(loweralkylimide).

20. The polyelectrolyte of claim 16 in which the copolymer is cross-linked with methyliminobispropylamine and the amine-imide is dimethylaminopropylimide.

21. The polyelectrolyte of claim 16 in which the alkoxyalkylamine is selected from the group consisting of methoxyethylamine and methoxypropylamine.

22. The polyelectrolyte of claim 16 in which the partial substitution with amine-imide ranges from about 2% to about 90% of the free carboxyl or anhydride sites.

* * * * *